US012745973B2

(12) United States Patent
Kojima et al.

(10) Patent No.: US 12,745,973 B2
(45) Date of Patent: Sep. 29, 2026

(54) PCCT APPARATUS AND CONTROL METHOD OF THE SAME

(71) Applicant: FUJIFILM Corporation, Tokyo (JP)

(72) Inventors: Shinichi Kojima, Tokyo (JP); Kazuma Yokoi, Tokyo (JP); Isao Takahashi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 141 days.

(21) Appl. No.: 18/969,309

(22) Filed: Dec. 5, 2024

(65) Prior Publication Data

US 2025/0235179 A1 Jul. 24, 2025

(30) Foreign Application Priority Data

Jan. 19, 2024 (JP) ................................ 2024-006633

(51) Int. Cl.
*A61B 6/58* (2024.01)
*A61B 6/03* (2006.01)
*A61B 6/42* (2024.01)

(52) U.S. Cl.
CPC .............. *A61B 6/585* (2013.01); *A61B 6/032* (2013.01); *A61B 6/4241* (2013.01); *A61B 6/583* (2013.01)

(58) Field of Classification Search
CPC ....... A61B 6/585; A61B 6/032; A61B 6/4241; A61B 6/583
See application file for complete search history.

(56) References Cited

U.S. PATENT DOCUMENTS

2013/0343508 A1* 12/2013 Hagiwara ............... G06T 12/20 378/4
2016/0239971 A1* 8/2016 Yu .......................... A61B 6/032

FOREIGN PATENT DOCUMENTS

JP 2019-058488 4/2019

OTHER PUBLICATIONS

KR 10-2024-0000901 A and its English translation (Year: 2024).*

* cited by examiner

*Primary Examiner* — Chih-Cheng Kao
(74) *Attorney, Agent, or Firm* — JCIPRNET

(57) ABSTRACT

Provided are a PCCT apparatus and a control method thereof capable of improving an interpolation accuracy related to substance discrimination and shortening a processing time. A PCCT apparatus includes: a scanner that rotates an X-ray source that irradiates a subject with X-rays and a photon counting detector that detects the X-rays transmitted through the subject for each of a plurality of energy bins around the subject; an image generation unit that generates a tomographic image using projection data calculated based on an output of the photon counting detector; a map creation unit that creates a calibration data map based on the number of X-ray photons transmitted through each of a plurality of calibration phantoms having a first basal substance and a second basal substance of which a material and a thickness are known; a region division unit that divides the calibration data map into a non-linear region and a linear region; and an interpolation unit that performs non-linear interpolation in the non-linear region and performs linear interpolation in the linear region.

6 Claims, 7 Drawing Sheets

PCCT APPARATUS AND CONTROL METHOD OF THE SAME

CLAIM OF PRIORITY

The present application claims priority from Japanese Patent Application JP 2024-006633 filed on Jan. 19, 2024, the content of which is hereby incorporated by reference into this application.

BACKGROUND OF THE INVENTION

1. Field of the Invention

The present invention relates to a photon counting computed tomography (PCCT) apparatus that is an X-ray CT apparatus comprising a photon counting detector, and particularly relates to interpolation processing of calibration data used for calibration of the photon counting detector.

2. Description of the Related Art

An X-ray CT apparatus uses projection data from multiple directions that is obtained by rotating, around a subject, an X-ray source that emits an X-ray to the subject and an X-ray detector that detects the X-ray transmitted through the subject to generate a tomographic image of the subject. The generated tomographic image is used as a medical image used for image diagnosis of the subject.

In the PCCT apparatus that uses a photon counting detector as an X-ray detector, the number of X-ray photons can be counted for each energy, and thus a substance in the subject can be discriminated by using projection values acquired in each of a plurality of energy bins. However, in a case where an X-ray dose incident on the photon counting detector is large, a non-linear phenomenon such as pile-up in which a plurality of X-ray signals are erroneously counted as a single X-ray with added energy or counting omission in which while an X-ray signal is being processed by a certain photon counting detector, another X-ray is incident, so that the X-ray signal is not processed and counted may occur, and a discrimination accuracy of a substance may be degraded.

JP2019-58488A discloses that, in an X-ray CT apparatus that counts the number of X-ray photons for each energy bin, a substance within a subject is discriminated based on an X-ray dose transmitted through the subject and an X-ray dose transmitted through a predetermined substance. In addition, it is disclosed that, in order to improve the discrimination accuracy, the same signal processing is performed on each of two X-ray doses a plurality of times, a condition in which an error between the two X-ray doses after the signal processing is smaller is selected, and the substance is discriminated based on a result of the signal processing under the selected condition. Further, it is disclosed that, in a case where an interval of transmission distances of the predetermined substance is rough, the interval of the transmission distances is interpolated with fine accuracy by parabola fitting, linear approximation, polynomial approximation, spline, bicubic, or the like.

SUMMARY OF THE INVENTION

However, in JP2019-58488A, consideration for interpolation based on non-linearity or linearity is insufficient. That is, in a case where linear interpolation is performed in a region where the non-linearity is strong, the interpolation accuracy is reduced, and in a case where non-linear interpolation is performed in a region where the linearity is strong, an amount of calculation increases and a processing time becomes longer.

Therefore, an object of the present invention is to provide a PCCT apparatus and a control method thereof capable of improving an interpolation accuracy related to substance discrimination and shortening a processing time.

In order to achieve the above object, according to an aspect of the present invention, there is provided a PCCT apparatus comprising: a scanner that rotates an X-ray source that irradiates a subject with X-rays and a photon counting detector that detects the X-rays transmitted through the subject for each of a plurality of energy bins around the subject; an image generation unit that generates a tomographic image using projection data calculated based on an output of the photon counting detector; a map creation unit that creates a calibration data map based on the number of X-ray photons transmitted through each of a plurality of calibration phantoms having a first basal substance and a second basal substance of which a material and a thickness are known; a region division unit that divides the calibration data map into a non-linear region and a linear region; and an interpolation unit that performs non-linear interpolation in the non-linear region and performs linear interpolation in the linear region.

In addition, according to another aspect of the present invention, there is provided a control method of a PCCT apparatus including a scanner that rotates an X-ray source that irradiates a subject with X-rays and a photon counting detector that detects the X-rays transmitted through the subject for each of a plurality of energy bins around the subject, and an image generation unit that generates a tomographic image using projection data calculated based on an output of the photon counting detector, the control method comprising: a map creation step of creating a calibration data map based on the number of X-ray photons transmitted through each of a plurality of calibration phantoms having a first basal substance and a second basal substance of which a material and a thickness are known; a region division step of dividing the calibration data map into a non-linear region and a linear region; and an interpolation step of performing non-linear interpolation in the non-linear region and performing linear interpolation in the linear region.

According to the present invention, it is possible to provide a PCCT apparatus and a control method thereof capable of improving an interpolation accuracy related to substance discrimination and shortening a processing time.

DESCRIPTION OF THE PREFERRED EMBODIMENTS

Figure 1:
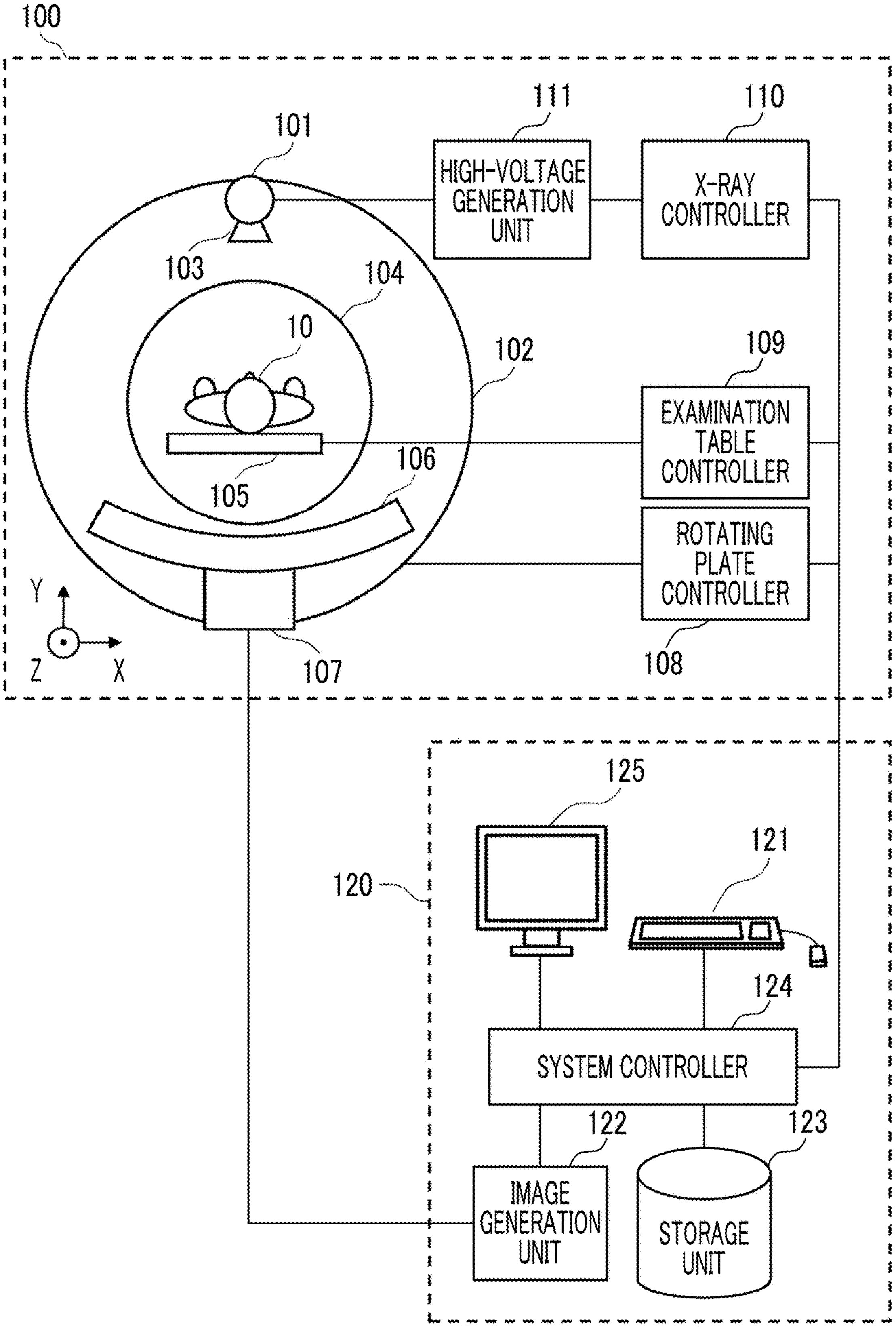
FIG. 1 is a diagram showing an overall configuration of a PCCT apparatus.

Hereinafter, examples of a photon counting computed tomography (PCCT) apparatus and a control method thereof according to the present invention will be described with reference to the accompanying drawings. In the following description and the accompanying drawings, components having the same functional configuration will be denoted by the same reference numerals, and duplicated descriptions will not be repeated.

Example 1

An overall configuration of a PCCT apparatus of Example 1 will be described with reference to FIG. 1. The PCCT apparatus comprises a scanner 100 and an operation unit 120. The scanner 100 is installed in an imaging room surrounded by a shielding material that blocks X-rays, and the operation unit 120 is installed in an operation room located outside the imaging room. A rotation axis direction of the scanner 100 is referred to as a Z-axis, a horizontal direction perpendicular to the Z-axis is referred to as an X-axis, and a vertical direction perpendicular to the Z-axis is referred to as a Y-axis.

The scanner 100 comprises an X-ray source 101, a rotating plate 102, a collimator 103, a photon counting detector 106, a data collection unit 107, an examination table 105, a rotating plate controller 108, an examination table controller 109, an X-ray controller 110, and a high-voltage generation unit 111. The X-ray source 101 is a device that irradiates a subject 10 placed on the examination table 105 with X-rays and is, for example, an X-ray tube device. The collimator 103 is a device that limits an irradiation range of X-rays. The rotating plate 102 includes an opening portion 104 through which the subject 10 placed on the examination table 105 enters, is equipped with the X-ray source 101 and the photon counting detector 106, and rotates the X-ray source 101 and the photon counting detector 106 around the subject 10.

The photon counting detector 106 is a device that is disposed to face the X-ray source 101 and acquires a spatial distribution of X-rays by comprising a plurality of detection elements that detect the X-rays. The detection elements of the photon counting detector 106 are arranged two-dimensionally in a rotation direction and a rotation axis direction of the rotating plate 102, individually count incident X-ray photons, and discriminate each X-ray photon into a plurality of energy bins.

The rotating plate controller 108 is a device that controls rotation and inclination of the rotating plate 102. The examination table controller 109 is a device that controls upward, downward, forward, backward, leftward, and rightward movements of the examination table 105. The high-voltage generation unit 111 is a power source that generates a tube voltage, which is a voltage applied to the X-ray source 101, and a tube current, which is a current supplied to the X-ray source 101. The X-ray controller 110 is a device that controls an output of the high-voltage generation unit 111. The rotating plate controller 108, the examination table controller 109, and the X-ray controller 110 are, for example, a micro-processing unit (MPU) or the like.

The operation unit 120 comprises an input unit 121, an image generation unit 122, a display unit 125, a storage unit 123, and a system controller 124. The input unit 121 is a device that is used to input examination data such as a name of the subject 10, an examination date and time, and an imaging condition, and is, for example, a keyboard, a pointing device, a touch panel, or the like. The image generation unit 122 is a device that generates a tomographic image by using digital data collected by the data collection unit 107, and is, for example, an MPU, a graphics processing unit (GPU), or the like. The display unit 125 is a device that displays the tomographic image or the like generated by the image generation unit 122, and is, for example, a liquid crystal display, a touch panel, or the like. The storage unit 123 is a device that stores the digital data collected by the data collection unit 107, the tomographic image generated by the image generation unit 122, a program to be executed by the system controller 124, data to be used by the program, and the like, and is, for example, a hard disk drive (HDD), a solid state drive (SSD), or the like. The system controller 124 is a device that controls each unit such as the rotating plate controller 108, the examination table controller 109, and the X-ray controller 110, and is, for example, a central processing unit (CPU).

With the generation of the tube voltage and the tube current by the high-voltage generation unit 111 based on the imaging condition set via the input unit 121, the X-rays according to the imaging condition are emitted from the X-ray source 101 to the subject 10. The photon counting detector 106 detects the X-rays emitted from the X-ray source 101 and transmitted through the subject 10 with multiple detection elements to acquire the spatial distribution of the transmitted X-rays. The rotating plate 102 is controlled by the rotating plate controller 108 and rotates based on the imaging condition input through the input unit 121, particularly a rotation speed or the like. The examination table 105 is controlled by the examination table controller 109 and moves relative to the rotating plate 102 to move an imaging position designated with respect to the subject 10 to an imaging field of view, which is a range in which the transmitted X-rays are detected.

With repetition of the emission of the X-rays by the X-ray source 101 and the detection of the X-rays by the photon counting detector 106 together with the rotation of the rotating plate 102, projection data of the subject 10 is measured at various projection angles. In the projection data, a view representing each projection angle is associated with a channel (ch) number and a column number which are detection element numbers of the photon counting detector 106. The measured projection data is transmitted to the image generation unit 122. The image generation unit 122 performs back-projection processing on a plurality of projection data to generate the tomographic image. The generated tomographic image is displayed on the display unit 125 or stored in the storage unit 123 as a medical image.

Since the PCCT apparatus comprising the photon counting detector 106 can acquire the projection data of the subject 10 for each energy bin, a medical image for each energy bin or a medical image discriminated into substances having different compositions can be generated. In order to obtain the medical image discriminated into the substances having different compositions, it is necessary to acquire calibration data of the photon counting detector 106 in advance.

Figure 2:
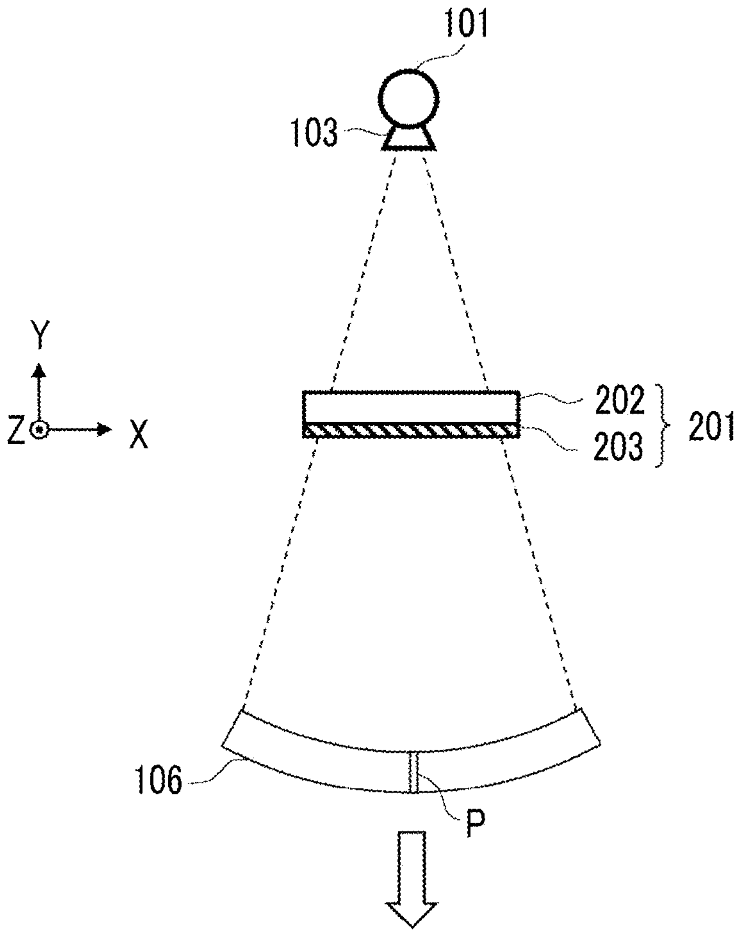
FIG. 2 is a diagram describing calibration data of a photon counting detector.
Figure 2:
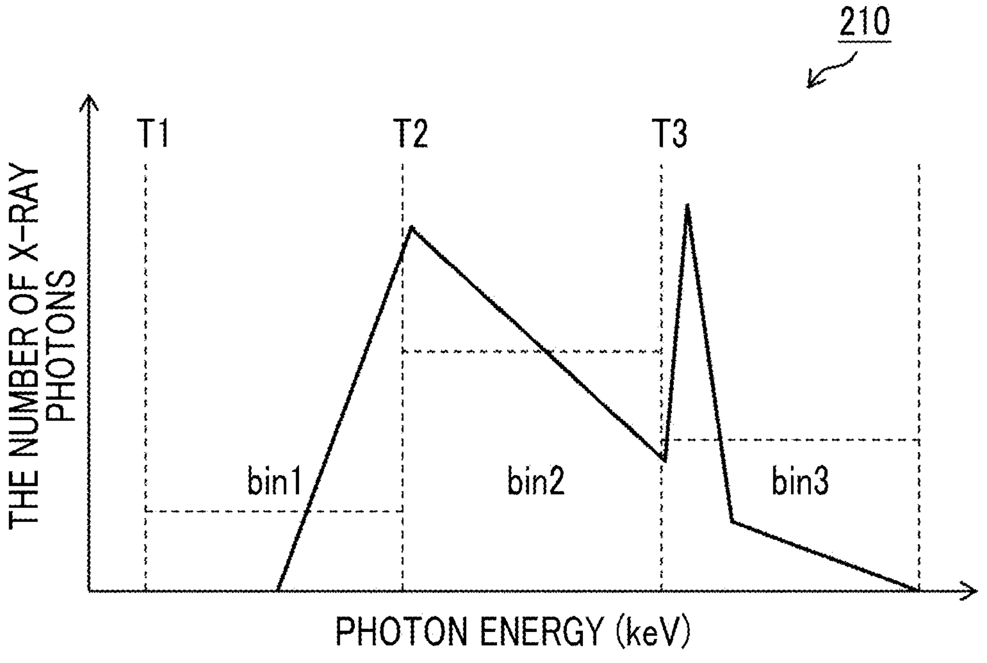

The calibration data 210 of the photon counting detector 106 will be described with reference to FIG. 2. The calibration data 210 is acquired by using a calibration phantom 201 including a first basal substance 202 and a second basal substance 203 which have known compositions and thicknesses. That is, the calibration data 210 corresponding to a photon energy spectrum illustrated in a lower part of FIG. 2 is acquired by counting the X-ray photons transmitted through the calibration phantom 201 by a detection element P of the photon counting detector 106 in each of the plurality of energy bins. FIG. 2 shows the number of X-ray photons divided and counted in three energy bins bin1, bin2, and bin3 which are respectively from T1 to T2, from T2 to T3, and from T3. The calibration data 210 is acquired in advance using each of a plurality of calibration phantoms 201 in which the thicknesses of the first basal substance 202 and the second basal substance 203 are different.

Figure 3:
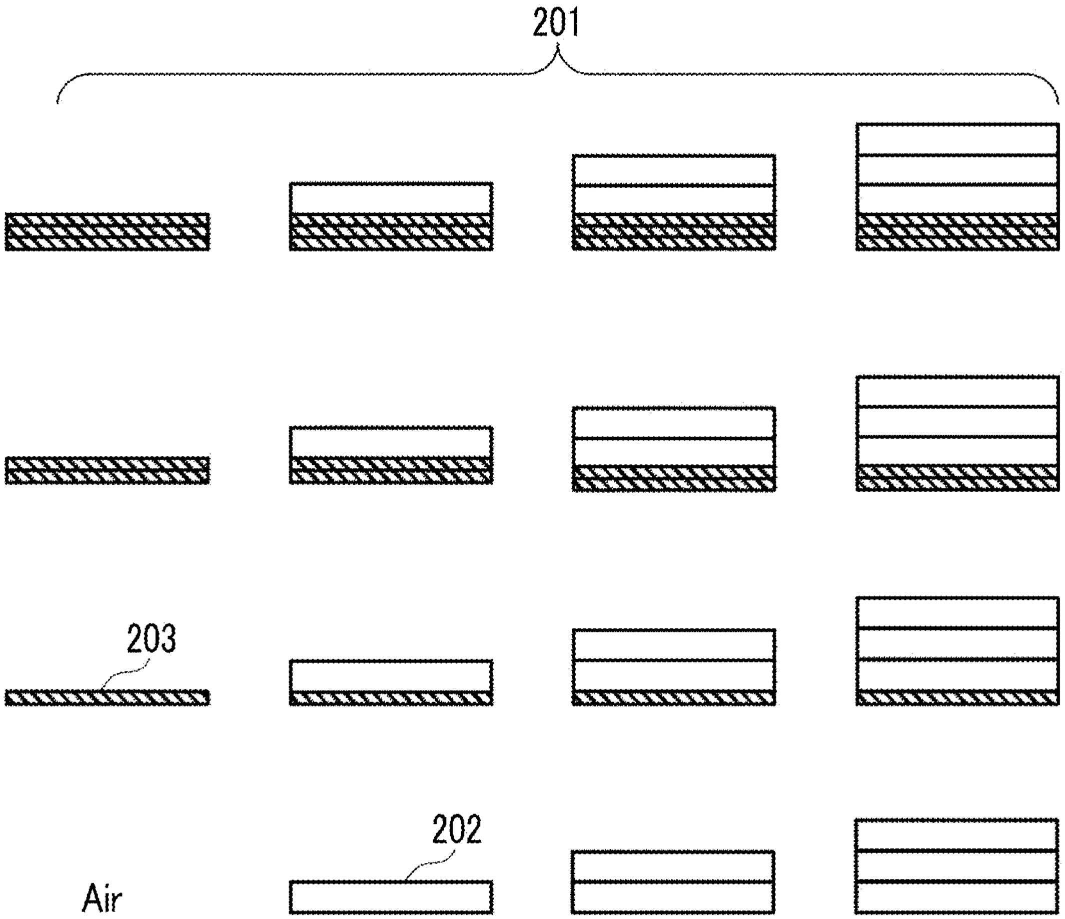
FIG. 3 is a diagram showing a configuration example of a calibration phantom.

An example of the plurality of calibration phantoms 201 will be described with reference to FIG. 3. FIG. 3 illustrates 16 types of calibration phantoms 201 in which the number of the first basal substance 202 and the number of the second basal substance 203 are different. That is, the calibration phantom 201 illustrated in FIG. 3 is a combination of 0 to 3 first basal substances 202 and 0 to 3 second basal substances 203. For the first basal substance 202, for example, an acrylic plate is used as a substance corresponding to a soft tissue of the subject 10. In addition, for the second basal substance 203, for example, a tin plate is used as a substance corresponding to an iodine contrast agent used in angiography. The first basal substance 202 may be a substance other than acrylic as long as it is a substance corresponding to water or a soft tissue. In addition, the second basal substance 203 may be silver other than tin as long as it is a substance corresponding to an iodine contrast agent, or may be aluminum or titanium corresponding to a bone of the subject 10, or other metals such as rhodium, palladium, lead, gold, platinum, tungsten, or alloys thereof.

The calibration data 210 acquired using the plurality of calibration phantoms 201 is compared with the projection data of the subject 10, and the calibration data 210 similar to a photon energy spectrum of the projection data of the subject 10 is extracted from a plurality of the calibration data 210. Then, the subject 10 is subjected to substance discrimination based on the thicknesses of the first basal substance 202 and the second basal substance 203 of the calibration phantom 201 corresponding to the extracted calibration data 210.

Since the calibration data 210 is acquired by using the calibration phantom 201 having a predetermined thickness, appropriate interpolation processing is required between a plurality of the calibration data 210. That is, in a case where linear interpolation is performed in a region where the non-linearity is strong, the interpolation accuracy is reduced, and in a case where non-linear interpolation is performed in a region where the linearity is strong, an amount of calculation increases and a processing time becomes longer. Therefore, in Example 1, a calibration data map, which is a set of the calibration data 210, is divided into a non-linear region and a linear region, the non-linear interpolation is performed in the non-linear region, and the linear interpolation is performed in the linear region.

An example of a flow of processing of dividing the calibration data map, which is a set of the calibration data 210, into the non-linear region and the linear region will be described for each step with reference to FIG. 4.

S401

The calibration phantom 201 is set between the X-ray source 101 and the photon counting detector 106.

S402

The system controller 124 counts the X-ray photons transmitted through the calibration phantom 201 while changing an X-ray dose emitted from the X-ray source 101. In S402, the rotating plate 102 is not rotated.

S403

Whether or not the counting for all the calibration phantoms 201 has been completed is determined. In a case where the counting for all the calibration phantoms 201 is completed, the process proceeds to S404. In a case where there is any uncounted calibration phantom 201, the process returns to S401, and the uncounted calibration phantom 201 is set between the X-ray source 101 and the photon counting detector 106.

S404

Figure 5:
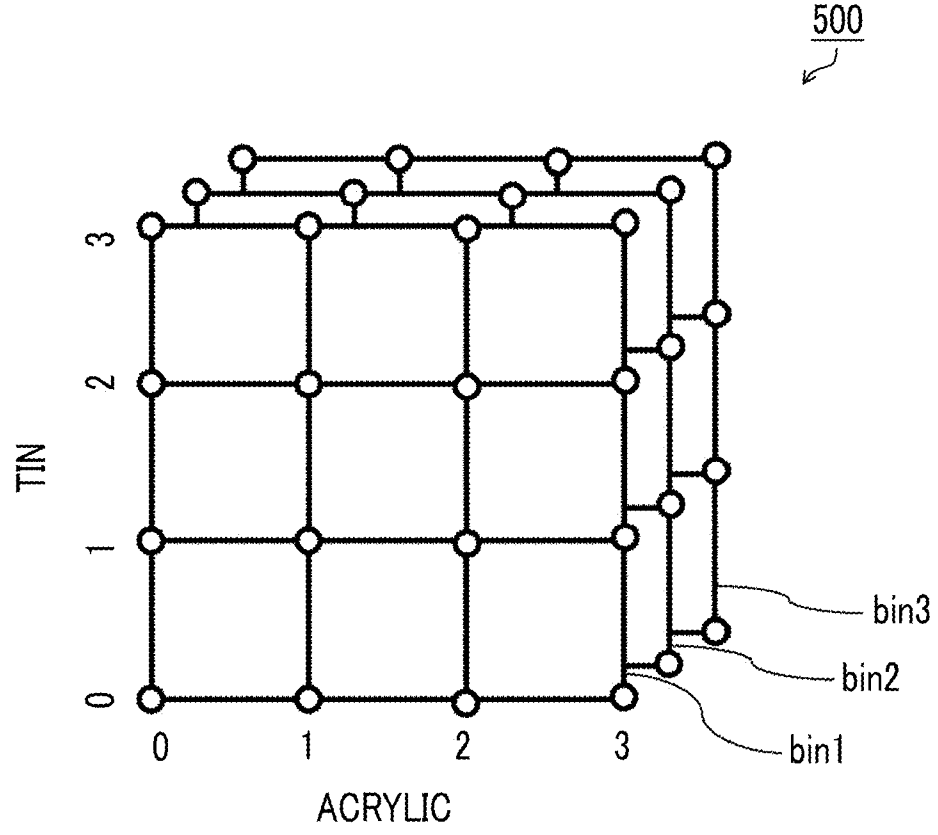
FIG. 5 is a diagram showing an example of a calibration data map.

The system controller 124 creates a calibration data map 500 illustrated in FIG. 5 based on a counting result in S402. The calibration data map 500 is a set of the calibration data 210 acquired for each of the calibration phantoms 201. The calibration data map 500 illustrated in FIG. 5 has the number of acrylic plates, which are the first basal substances 202, on a horizontal axis and the number of tin plates, which are the second basal substances 203, on a vertical axis, and is created for each energy bin. One white circle in FIG. 5 corresponds to one of the calibration phantoms 201 illustrated in FIG. 3 and includes the calibration data 210 for each of a plurality of irradiation doses.

S405

Figure 6:
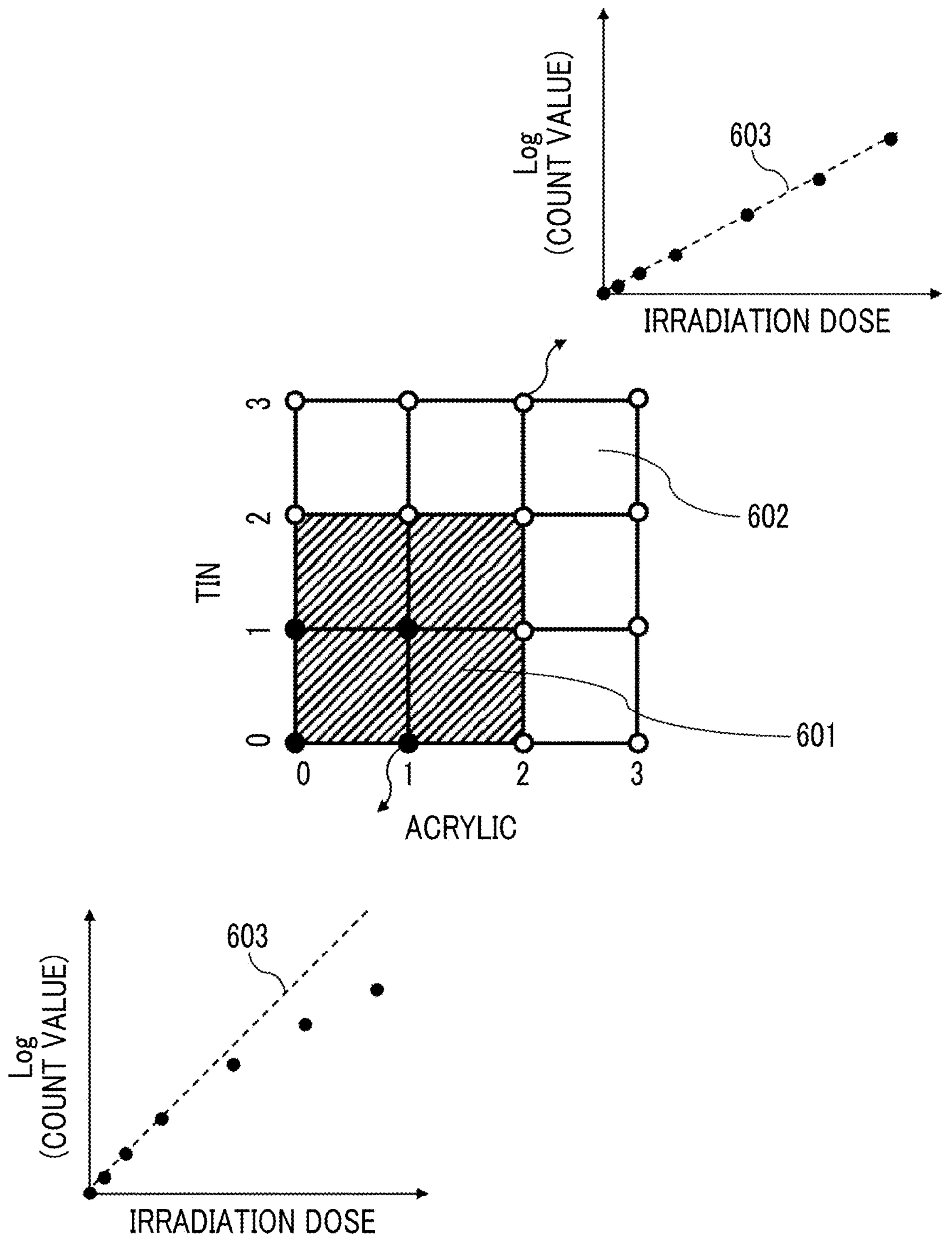
FIG. 6 is a diagram describing region division of the calibration data map.

The system controller 124 divides the calibration data map 500 created in S404 into two regions of a non-linear region 601 and a linear region 602 illustrated in FIG. 6. The region division of the calibration data map 500 is performed based on the linearity of a Log value of a count value of transmitted photons for each of the plurality of irradiation doses. That is, in a graph in which the Log value of the count value is plotted on a vertical axis and the irradiation dose is plotted on a horizontal axis, a region including non-linear data in which a difference between a reference straight line 603 and the Log value of the count value is larger than a predetermined threshold value is set as the non-linear region 601, and a region not including the non-linear data is set as the linear region 602. In FIG. 6, the non-linear data is shown by black circles, and the non-linear region 601 is shown by diagonal lines. The reference straight line 603 is calculated based on the thickness of each of the first basal substance 202 and the second basal substance 203 included in the calibration phantom 201. Further, the threshold value is determined based on the discrimination accuracy.

Figure 4:
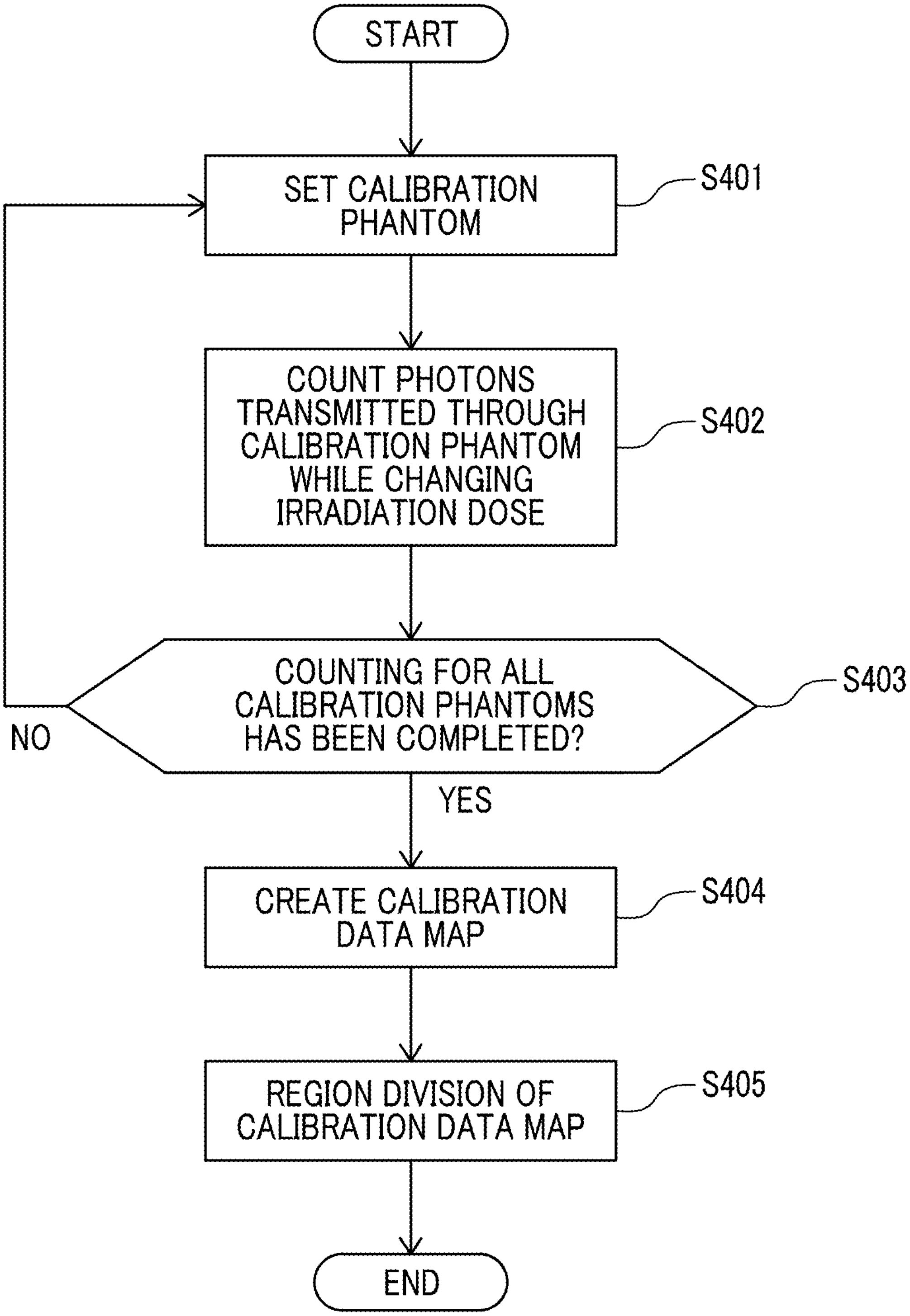
FIG. 4 is a diagram showing an example of a flow of processing of Example 1.

The calibration data map 500 is divided into the non-linear region 601 and the linear region 602 by the flow of processing illustrated in FIG. 4. The calibration data map 500 divided into the non-linear region 601 and the linear region 602 is stored in the storage unit and is used for the substance discrimination of the subject 10. The system controller 124 that executes S404 functions as a map creation unit that creates the calibration data map 500 based on the number of X-ray photons transmitted through each of the plurality of calibration phantoms 201 having the first basal substance 202 and the second basal substance 203 of which a material and a thickness are known. In addition, the system controller 124 that executes S405 functions as a region division unit that divides the calibration data map 500 into the non-linear region 601 and the linear region 602.

Figure 7:
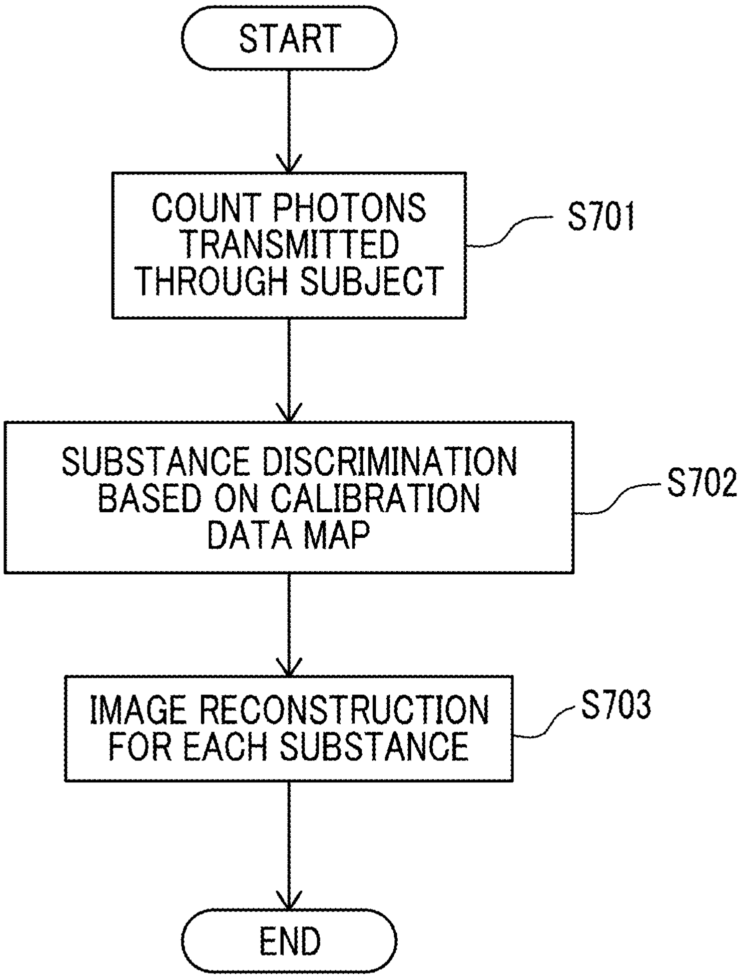
FIG. 7 is a diagram showing an example of a flow of processing of generating a tomographic image in which a substance is discriminated.

An example of a flow of processing of generating a tomographic image in which a substance is discriminated based on the calibration data map 500 will be described for each step with reference to FIG. 7.

S701

The projection data of the subject 10 is acquired through the control of the system controller 124. More specifically, in a state in which the rotating plate 102 is rotated, the subject 10 is irradiated with X-rays from the X-ray source 101, and the X-rays transmitted through the subject 10 are detected by the photon counting detector 106, so that the projection data at various projection angles are acquired. The projection data of the subject 10 is acquired while being divided into a plurality of energy bins.

S702

The system controller 124 discriminates the projection data of the subject 10 acquired in S701 into a plurality of substances, for example, the first basal substance 202 and the second basal substance 203, based on the calibration data map 500 read out from the storage unit. In a case of substance discrimination, the non-linear interpolation is performed in the non-linear region 601, and the linear interpolation is performed in the linear region 602. For the non-linear interpolation in the non-linear region 601, for example, a high-order function is used, and it is preferable that the order of the high-order function is increased according to the strength of the non-linearity. As the non-linearity is stronger, the order is increased, and thus an interpolation accuracy can be further improved. In addition, in the linear region 602, it is preferable that the linear interpolation is performed based on a statistical error of the Log value of the count value. By performing the linear interpolation based on the statistical error, the interpolation accuracy can be further improved.

S703

The system controller 124 reconstructs the tomographic image for each substance using the projection data subjected to the substance discrimination in S702. That is, the tomographic image of the first basal substance 202 and the tomographic image of the second basal substance 203 are reconstructed.

The tomographic image of the subject 10 is generated for each substance using the projection data subjected to the substance discrimination based on the calibration data map 500 according to the flow of processing described with reference to FIG. 7. Since the calibration data map 500 divided into the non-linear region 601 and the linear region 602 is used for the substance discrimination, the non-linear interpolation is performed in the non-linear region 601, and the linear interpolation is performed in the linear region 602, it is possible to improve the interpolation accuracy related to the substance discrimination and to shorten the processing time. The system controller 124 that executes S702 functions as an interpolation unit that performs the non-linear interpolation in the non-linear region 601 and performs the linear interpolation in the linear region 602.

The examples of the present invention have been described above. The present invention is not limited to the above examples, and the components can be modified and embodied without departing from the spirit of the invention. In addition, a plurality of the components disclosed in the above examples may be combined as appropriate. Further, some components may be deleted from all the components shown in the above examples.

EXPLANATION OF REFERENCES

10: subject
100: scanner
101: X-ray source
102: rotating plate
103: collimator
104: opening portion
105: examination table
106: photon counting detector
107: data collection unit
108: rotating plate controller
109: examination table controller
110: X-ray controller
111: high-voltage generation unit
120: operation unit
121: input unit
122: image generation unit
123: storage unit
124: system controller
125: display unit
201: calibration phantom
202: first basal substance
203: second basal substance
210: calibration data
500: calibration data map
601: non-linear region
602: linear region
603: reference straight line

What is claimed is:

1. A PCCT apparatus comprising:
a scanner that rotates an X-ray source that irradiates a subject with X-rays and a photon counting detector that detects the X-rays transmitted through the subject for each of a plurality of energy bins around the subject;
an image generation unit that generates a tomographic image using projection data calculated based on an output of the photon counting detector;
a map creation unit that creates a calibration data map based on the number of X-ray photons transmitted through each of a plurality of calibration phantoms having a first basal substance and a second basal substance of which a material and a thickness are known;
a region division unit that divides the calibration data map into a non-linear region and a linear region; and
an interpolation unit that performs non-linear interpolation in the non-linear region and performs linear interpolation in the linear region.

2. The PCCT apparatus according to claim 1,
wherein the region division unit performs region division based on linearity of a Log value of a count value of photons transmitted through the calibration phantom with respect to an irradiation dose onto the calibration phantom.

3. The PCCT apparatus according to claim 2,
wherein the region division unit sets a region including non-linear data in which a difference between a reference straight line calculated based on the thickness of the first basal substance and the thickness of the second basal substance and the Log value is larger than a predetermined threshold value, as the non-linear region, and sets a region not including the non-linear data, as the linear region.

4. The PCCT apparatus according to claim 1,
wherein the interpolation unit uses a high-order function for the non-linear interpolation, and increases an order of the high-order function as non-linearity of the non-linear region is stronger.

5. The PCCT apparatus according to claim 1,
wherein the interpolation unit performs the linear interpolation based on a statistical error of a Log value of a count value of photons transmitted through the calibration phantom.

6. A control method of a PCCT apparatus including a scanner that rotates an X-ray source that irradiates a subject with X-rays and a photon counting detector that detects the X-rays transmitted through the subject for each of a plurality of energy bins around the subject, and an image generation unit that generates a tomographic image using projection data calculated based on an output of the photon counting detector, the control method comprising:

a map creation step of creating a calibration data map based on the number of X-ray photons transmitted through each of a plurality of calibration phantoms having a first basal substance and a second basal substance of which a material and a thickness are known;

a region division step of dividing the calibration data map into a non-linear region and a linear region; and an interpolation step of performing non-linear interpolation in the non-linear region and performing linear interpolation in the linear region.

* * * * *